United States Patent
Liu et al.

(10) Patent No.: US 11,124,832 B2
(45) Date of Patent: Sep. 21, 2021

(54) SERUM MIRNA MARKER FOR OPLL DIAGNOSIS AND APPLICATION THEREOF

(71) Applicant: THE SECOND MILITARY MEDICAL UNIVERSITY, Shanghai (CN)

(72) Inventors: Yang Liu, Shanghai (CN); Chen Xu, Shanghai (CN); Hao Zhang, Shanghai (CN); Wen Yuan, Shanghai (CN); Peng Cao, Shanghai (CN); Huiqiao Wu, Shanghai (CN); Yuanyuan Chen, Shanghai (CN); Xiaolong Shen, Shanghai (CN)

(73) Assignee: THE SECOND MILITARY MEDICAL UNIVERSITY, Shanghai (CN)

( * ) Notice: Subject to any disclaimer, the term of this patent is extended or adjusted under 35 U.S.C. 154(b) by 419 days.

(21) Appl. No.: 16/063,195

(22) PCT Filed: Dec. 7, 2016

(86) PCT No.: PCT/CN2016/000675
§ 371 (c)(1),
(2) Date: Jun. 15, 2018

(87) PCT Pub. No.: WO2017/101172
PCT Pub. Date: Jun. 22, 2017

(65) Prior Publication Data
US 2019/0002983 A1    Jan. 3, 2019

(30) Foreign Application Priority Data
Dec. 15, 2015 (CN) .......................... 201510936874.2

(51) Int. Cl.
*C12P 19/34* (2006.01)
*C12Q 1/6883* (2018.01)
*C12Q 1/68* (2018.01)

(52) U.S. Cl.
CPC ............. *C12Q 1/6883* (2013.01); *C12Q 1/68* (2013.01); *C12Q 2600/158* (2013.01); *C12Q 2600/178* (2013.01)

(58) Field of Classification Search
CPC .................................................... C12Q 1/6883
See application file for complete search history.

(56) References Cited

U.S. PATENT DOCUMENTS

| | | | | |
|---|---|---|---|---|
| 2012/0058915 | A1* | 3/2012 | Croce | A61P 35/00 506/9 |
| 2013/0109741 | A1* | 5/2013 | Berezikov | C12Q 1/6809 514/44 A |
| 2016/0090636 | A1* | 3/2016 | Ju | C12Q 1/6886 506/9 |

FOREIGN PATENT DOCUMENTS

| | | |
|---|---|---|
| CN | 101368213 A | 2/2009 |
| CN | 101386848 A | 3/2009 |
| CN | 102725632 A | 10/2012 |
| CN | 102933719 A | 2/2013 |
| CN | 103205430 A | 7/2013 |
| CN | 103614468 A | 3/2014 |
| CN | 105400882 A | 3/2016 |
| WO | WO2015153909 A2 | 10/2015 |

OTHER PUBLICATIONS

Wang, H. et al., "Association of bone morphogenetic protein-2 gene polymorphisms with susceptibility to ossification of the posterior longitudinal ligament of the spine and its severity in Chinese patients" Eur. Spine Journal, Apr. 4, 2008, pp. 956-964, vol. 17.

* cited by examiner

*Primary Examiner* — Kenneth R Horlick
(74) *Attorney, Agent, or Firm* — Muncy, Geissler, Olds and Lowe, P.C.

(57) ABSTRACT

A serum microRNA (miRNA) marker suitable for early screening and diagnosis of ossification of posterior longitudinal ligament (OPLL) and its application in the diagnostic reagent or kit for the OPLL. Biomarker miRNA-563, miRNA-196b, miRNA-10a and miRNA-129 have high diagnostic value for OPLL, and the development and application of the related serum miRNA biomarker detection reagent kit. It can be applied in the screening of ossification of posterior longitudinal ligament disease, supporting the diagnosis of OPLL more quickly and accurately, evaluate the patient's ossification condition, and may lay down the foundation for improving clinical therapeutic effect.

4 Claims, 5 Drawing Sheets
Specification includes a Sequence Listing.

SERUM MIRNA MARKER FOR OPLL DIAGNOSIS AND APPLICATION THEREOF

BACKGROUND OF THE INVENTION

1. Field of the Invention

The invention relates to the technical field of medical biological detection, in particular, it is a serum miRNAs marker and detection application suitable for early screening and diagnosis of ossification of posterior longitudinal ligament (OPLL).

2. Description of the Related Art

The ossification of the posterior longitudinal ligament (OPLL) is one of the common spinal disorders. The ossification of the ligament causes spinal cord compression, thus causing the sensory, movement and sphincter dysfunction of the extremities and torso, and eventually leads to the paralysis of the limbs and the incontinence, which is a serious harm to human health. OPLL is especially common among Asian people. The incidence rate in Japan is 1.9 to 4.3% (Stapleton C J, Pham M H, Attenello F J, et al. Ossification of the posterior longitudinal ligament: genetics and pathophysiology [J]. Neurosurg Focus, 2011, 30(3): E6.).

Because ossification material is hard, decompression surgery has great risk, and it is easy to cause serious complications such as paralysis due to spinal cord injury. In the diagnosis, the early onset symptom often comes from the compression of the spinal nerve root, which is easily confused with other spinal cord diseases and misdiagnosis. From the treatment point of view, the surgical treatment is a huge challenge for spinal surgery because of the wide range of ossification, the heavy compression of the spinal cord, and the small space of the spinal canal.

Because the bony ossification of ligament is hard in nature, decompression surgery to treat it has great risk in injury nearby nerves, and it is easy to cause serious complications such as paralysis due to spinal cord injury. In the diagnosis, the early onset symptom often comes from the compression of the spinal nerve root, which is easily confused with other spinal cord diseases and often misdiagnosed. From the treatment point of view, the surgical treatment is a huge challenge for spinal surgery because of the wide range of ossification, the heavy compression of the spinal cord, and the small space of the spinal canal (Seichi A, Hoshino Y, Kimura A, et al. Neurological complications of cervical laminoplasty for patients with ossification of the posterior longitudinal ligament-a multi-institutional retrospective study. Spine (Phila Pa 1976). 2011, 36(15):E998-1003.). Therefore, it is an urgent problem to find early screening biomarkers with high sensitivity and specificity for the diagnosing of Ossification of Posterior Longitudinal Ligament.

In recent years, with the further development of the human genome project, a large number of non-coding sequences have attracted more attention, among which the discovery of microRNA (miRNA) is the most attractive. MiRNA is a class of non-coding short chain nucleotide fragments with a full length of only 20-24 bp, and is conservative in evolution. It plays a wide role in growth, tumorigenesis, immune response and so on. Because the action of miRNA is based on the specificity of the target site sequence, a miRNA may act on multiple mRNA, and a mRNA may be regulated by multiple miRNAs. The absence of individual miRNA may have no obvious influence on the development and survival of the organism, but it has its role in the occurrence of certain diseases (Flynt A S, Lai E C. Biological principles of microRNA-mediated regulation: shared themes amid diversity. Nat Rev Genet. 2008, 9(11): 831-842.). Because of the specificity of miRNA's action, it plays a crucial role in many chronic diseases, and is expected to become an important candidate marker for the occurrence, diagnosis and prognosis of major diseases (Ceribelli A, Nahid M A, Satoh M, et al. MicroRNAs in rheumatoid arthritis. FEBS Lett. 2011, 585(23):3667-74.).

It has been proved that miRNA is stable in the peripheral blood and has significant disease specificity, but its content is low and its detection is not easy. Therefore, the development of easy to detect, low cost, fast and effective detection kit can effectively improve the detection efficiency and achieve good repeatability. However, until now there is no report on the early screening of the Ossification of Posterior Longitudinal Ligament with serum miRNA. It is of great significance for the early diagnosis of the ossification of the posterior longitudinal ligament of every patient if we can screen out the serum miRNA as a biomarker for the abnormal expression of OPLL and develop the corresponding screening kit.

SUMMARY OF THE INVENTION

The primary purpose of the invention is to propose a set of serum miRNA markers related to Ossification of Posterior Longitudinal Ligament in view of the above problems.

In order to solve the above technical problems, the first aspect of the present invention provides a serum miRNAs marker suitable for early screening and diagnosis of ossification of the posterior longitudinal ligament, including miRNA-563, miRNA-196b, miRNA-10a, and miRNA-129.
miRNA-563' Accession number: MIMAT0003227' Sequence: agguugacauacguuuccc (SEQ ID NO: 1).
miRNA-196b' Accession number: MIMAT0001080' Sequence: uagguaguuuccuguuguuggg (SEQ ID NO: 2).
miRNA-10a' Accession number: MIMAT0000253' Sequence: uacccuguagauccgaauuugug (SEQ ID NO: 3).
miRNA-129' Accession number: MIMAT0000242' Sequence: cuuuuugcggucugggcuugc (SEQ ID NO: 4).

The expression levels of miRNA-563, miRNA-196b, miRNA-10a and miRNA-129 in serum are positively correlated with OPLL. Therefore, the risk and degree of OPLL in the population can be evaluated by detecting the expression level of miRNA-563, miRNA-196b, miRNA-10a and miRNA-129 in the serum.

The second aspect of the invention provides the application of the above serum miRNA markers in the diagnosis reagent or kit for diagnosing OPLL. Preferably, the diagnostic reagent or reagent kit is a serological test reagent or a detection kit.

The diagnostic reagent or reagent kit detects the expression amount of one or more than two kinds of miRNA in miRNA-563, miRNA-196b, miRNA-10a and miRNA-129 in biological samples. The biological samples are selected from fresh tissues or cells, formalin fixed or paraffin embedded tissues or cells, blood or body fluids. Preferably, the biological sample described is serum.

The diagnostic reagents or kits include: one or more specific probes, gene chips, or PCR primers for one of miRNA-563, miRNA-196b, miRNA-10a, miRNA-129, or more than two.

Preferably, the diagnostic reagent or reagent kit is a reagent or kit for detecting the expression level of miRNA using the Real-time RT-PCR (qPCR) method.

It is preferred that the nucleotide sequences of the specific PCR primers for miRNA-563, miRNA-196b, miRNA-10a, and miRNA-129 detection is shown in SEQ ID NO: 5, SEQ ID NO: 6, SEQ statements respectively.

The third aspect of the present invention provides a kit for the diagnosis of OPLL, including the reagent for detecting the amount of miRNA expression, which is selected from one or more of the miRNAs in miRNA-563, miRNA-196b, miRNA-10a, miRNA-129.

Preferably, the reagent used to detect the expression level of miRNA is a reagent for detecting the expression level of miRNA by Real-time RT-PCR method.

Preferably, the said kit includes: the nucleotide sequence of the specific PCR primers for miRNA-563, miRNA-196b, miRNA-10a, and miRNA-129 such as stated in SEQ ID NO: 5, SEQ ID NO: 6, SEQ ID NO: 7, SEQ ID NO: 8.

In the fourth aspect of the present invention, the usage of the reagents for detecting miRNA-563, miRNA-196b, miRNA-10a and miRNA-129 expression levels in the diagnosis or screening of OPLL is provided.

In fifth aspects of the present invention, the primers, such as SEQ ID NO: 5, SEQ ID NO: 6, SEQ ID NO: 7, SEQ ID NO: 8, are used in the preparation of a kit for the diagnosis or screening of OPLL.

By detecting the expression level of miRNA-563, miRNA-196b, miRNA-10a and miRNA-129, the present invention can be used in screening the onset risk of OPLL for the people detected: if the expression level of any miRNA in miRNA-563, miRNA-196b, miRNA-10a and miRNA-129 is higher than that of the normal value, the onset risk of OPLL is higher (the normal range of the miRNA is 6649±1554, 1800±901' 63717±17258' 1075±651 copies per 500 microliter peripheral venous blood serum respectively). And the expression level of any miRNA in miRNA-563, miRNA-196b, miRNA-10a and miRNA-129 was lower than the normal range in turn, the risk of OPLL is low (the range of normal values of the above miRNA was 1800±901' 6649±1554' 63717±17258' 1075±651 copies per 500 microliter peripheral blood venous serum respectively).

The technical schemes of the invention include: (1) establishing a unified standard sample collection and processing procedure, that is, standardized operation procedure (SOP); (2) establishing a system for the sampling process of the clinical information and storage procedures of the data for the patients to be measured; (3) the development of a sera miRNA screening kit, according to the ossification of the posterior longitudinal ligament and the healthy control, the specific serum miRNA standards and developed miRNA detection values for OPLL epidemiological screening kit.

The invention can be used to screen the risk and applied in early diagnosis of OPLL. By detecting the serum content of the above miRNA, the invention also uses the linear regression model to form a formula that combines the four miRNAs (the copy number of miRNA-563 per 500 microliter peripheral*0.04+the copy number of miRNA-196b per 500 microliter peripheral venous blood serum*0.03+the copy number of miRNA-10a per 500 microliter peripheral venous blood serum*0.004+the copy number of miRNA-129 per 500 microliter peripheral venous blood serum*0.05-353) and obtained the new fitting value. If the new value is greater than 0, then the patient can be diagnosed with OPLL. This application can be used for early screening and diagnosis of OPLL.

The benefit of the invention is that it is the first discovered biomarkers of OPLL using serum miRNA-563, miRNA-196b, miRNA-10a and miRNA-129 detection. The development and application of the serum miRNA markers and diagnostic kit can make the early screening of the posterior longitudinal ligament ossification more convenient and accurate. It provides a quick and accurate grasp of the patient's condition for clinicians to provide a basis for improving the effect of clinical treatment and to provide help for the discovery of a new small molecular drug target with potential therapeutic value.

BRIEF DESCRIPTION OF THE DRAWINGS

FIG. 5 shows the results of ROC analysis for markers shown in FIG. 4. It can be seen that each of the 4 miRNA has a certain specificity, and the results are all significant (P<0.05). The absolute quantitative values of four miRNAs were analyzed further using logistic multiple factor regression analysis to generate a new fitting value. The fitting value of four miRNAs was generated, and the pseudo value was tested by ROC. The results showed that the specificity of fitting value was higher than that of any single miRNA (P<0.01). The results suggest that the miRNAs can provide important reference value for the diagnosis of OPLL. Among them, the fitting values of miRNAs after logistic regression can reach a higher diagnostic specificity.

DESCRIPTION OF THE PREFERRED EMBODIMENTS

Practical Uses

The following specific embodiments provided by the invention are explained in detail with examples.

The reagent and raw materials used in the invention can be obtained commercially or can be prepared according to the literature method. The experimental methods that do not specify the specific conditions in the following embodiments are usually based on the conditions described in the conventional conditions such as 'Molecular Cloning: the laboratory guide' (New York: Cold Spring Harbor Laboratory Press, 1989), or in accordance with the conventional conditions, or the conditions recommended by the manufacturer.

Sample Case 1

1. Sample Collection

The posterior longitudinal ligament tissue (n=3) of the patients with OPLL and the normal posterior longitudinal ligament tissue (n=3) in the trauma operation were sequenced and the bioinformatics analysis of group miRNA was carried out. There was no significant difference in age, smoking, drinking and other factors between case group and control group (P>0.05).

2. Methods 2.1. The ligament tissues of the patients were immediately transferred to RNA later (Ambion company or other equivalent products) for cryo preservation. After being transported to the laboratory, cryopreservation at −80 C immediately.

2.2. After the sample was collected, the well preserved tissue samples were given to the company (high flux sequencing company, such as fierce ice information, bihao biology, etc.) to carry out the RNA extraction, library construction and quality inspection for further high throughput RNA sequencing.

2.3. The sample passed the quality inspection is put to library construction and sequenced using the Hiseq2000 (Illumina company) or above platform.

2.4. After the sequencing, data were annotated and homogenized. The miRNAs that had obvious differences between the case group and the control group was screened, and the 10 miRNA with the highest fold changes (FDR<0.5) were selected for subsequent verification.

2.5. The candidate miRNA was validated in 6 additional ossification tissues of posterior longitudinal ligament and normal ligament tissues.

2.6. In order to find out the diagnostic significance of the candidate miRNAs in peripheral blood samples, 10 cases of ossification of posterior longitudinal ligament and 10 normal human venous blood were used. Blood samples were 500×g centrifuged after blood coagulation at room temperature, 500 microliter serum were used for miRNA collection, reverse transcription and detection.

3. Results

Figure 1:
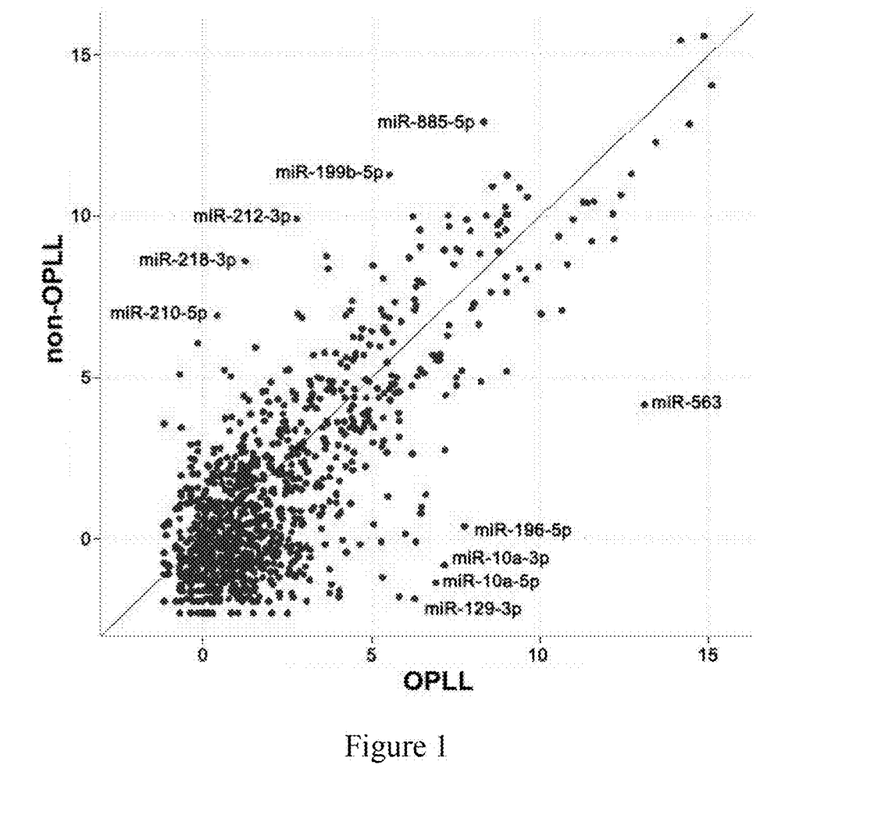
FIG. 1 showed high throughput miRNA sequencing after analyzing the miRNA mean values of the control group (the non ossified posterior longitudinal ligament tissue) and the case group (the tissue of the patients with ossification of the posterior longitudinal ligament), showing the differential expression of miRNAs. Among which, the 10 miRNA with the highest fold changes (marked by black font) is used as a candidate miRNA for subsequent verification.
Figure 2:
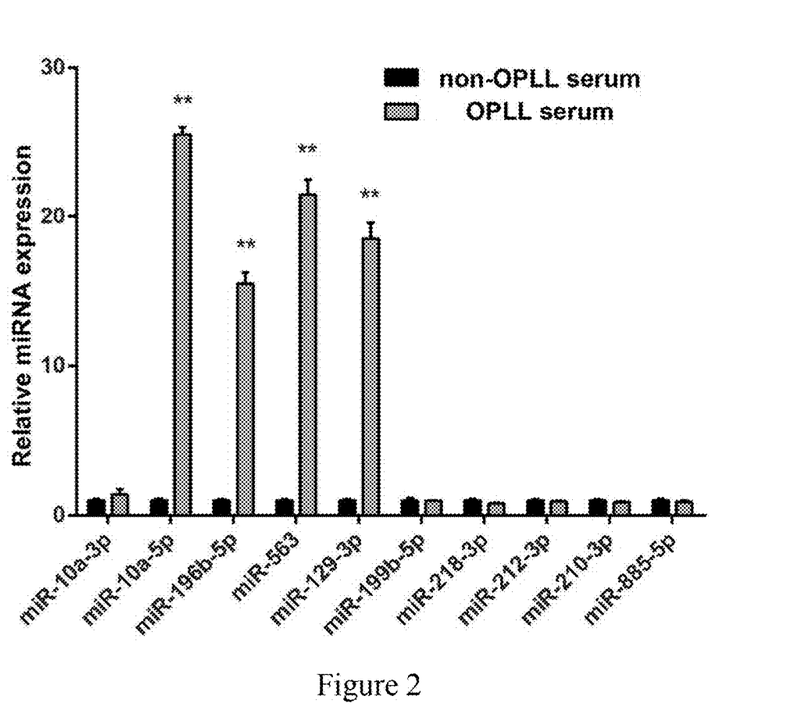
FIG. 2. Serum levels of candidate miRNAs in serum from 10 patients with ossification of ossification of posterior longitudinal ligament and 10 patients without ossification of posterior longitudinal ligament were detected. The real-time PCR method was used to analyze the miRNA expression, and we can see that the expression of miRNA-563, miRNA-196b, miRNA-10a and miRNA-129 in the serum of ossification patients was significantly higher than that of the control group, suggesting that the 4 miRNAs may be of diagnostic value. **, P<0.01.

High throughput sequencing and bioinformatics analysis were used to screen the differentially expressed miRNAs of OPLL, and 10 miRNA with the highest fold changes were selected as candidates, as shown in FIG. 1. Candidate miRNAs were validated at the histological level, and then serum miRNA was detected in patients with OPLL and normal patients. As shown in FIG. 2, the 10 differences of miRNA-563, miRNA-196b, miRNA-10a and miRNA-129 in the serum of patients with OPLL were significantly higher than that of in the normal human serum, suggesting that miRNA-563, miRNA-196b, miRNA-10a and miRNA-129 may be specified serological to OPLL.

Sample Case 2: Screening of Serum OPLL Specific miRNA for Inpatients

1. Sample Collection

The case group contains 36 samples collected in Shanghai Changzheng Hospital from June 2015 to September 2015, all of them were diagnosed with OPLL after CT three-dimensional reconstruction of the cervical spine or thoracic spine, no treatment was performed before collecting the blood. In the control group, 30 healthy individuals were screened for community disease during the same period. All patients were informed of the purpose of collection and the consent was signed of each patient before collection. There was no significant difference in age, smoking, drinking and other factors between case group and control group (P>0.05).

2. Methods 2.1. In the morning, the EDTA anticoagulant tube was used to extract 5 ml venous blood from the elbow. After collecting the blood, gently mixed, and the anticoagulant was mixed evenly with the blood. After 40 min at room temperature, samples were centrifuged at 1800 rpm 20 min, and the serum was separated from the blood cells, loaded into the 1.5 ml EP tube, and −80° C. preserved.

2.2. Takara RNAiso (Takara company) or TRIzol Reagent (Life Technology provided, or equal phenol chloroform RNA extraction reagents) was added to 500 microliter serum samples to a total volume of 1.2 ml, and placed 10 min at room temperature (about 25° C.) to ensure complete cracking; chloroform (0.2 ml chloroform/each extract reagents) was added and violently mixed for 15 s. After 5 min concussion at room temperature, the upper water phase contains the required RNA. Samples were centrifuged at 13000×g with low temperature for 15 min, the upper layer of clarified water is carefully sucked out of with no ribozyme tip, and added to isopropanol, with thorough mixing at room temperature for more than 15 min. Then centrifuged again at 13000×g with low temperature for 10 min. Careful retention of precipitation and discarding the supernatant, adding 75% (V/V) ethanol (1 ml 75% ethanol/ml lysate) to wash and centrifuged at 7500×g with low temperature for 5 min. Carefully discard the supernatant and dry 5 min in the air (notice that RNA cannot be excessively dry, or will affect its dissolution). To dissolve the total RNA by adding 14 μl preheated DEPC water, and adding the 1 microliter synthesized nematode miRNA cel-miR-39 (5'-UCACCGGGU-GUAAAUCAGCUUG-3', 10 nM, SEQ ID NO:10) as the external reference to each sample directly. Stored in 4° C. refrigerator for further reverse transcription.

2.3. Real-time RT-PCR (qPCR)

(1) The total RNA of the subjects was obtained. The reverse transcriptase (20 μl total) was prepared using TOYOBO ReverTra reverse transcriptase Kit (or similar product), and cDNA samples were obtained by reverse transcriptase 15 min through a water bath (or under the same environment).

(2) Primer design' reverse transcribe primers were listed miR-563 Reverse Transcribe Primer:

```
                                              (SEQ ID NO: 5)
GTCGTATCCAGTGCGAACTGTGGCGATCGGTACGGGCTACACTCGGCAA
TTGCACTGGATACGACGGGAA
``` miR-196b Reverse Transcribe Primer:

```
                                              (SEQ ID NO: 6)
GTCGTATCCAGTGCGAACTGTGGCGATCGGTACGGGCTACACTCGGCAA
TTGCACTGGATACGACCCCAA
``` miR-10a Reverse Transcribe Primer:

(SEQ ID NO: 7)
GTCGTATCCAGTGCGAACTGTGGCGATCGGTACGGGCTACACTCGGCAA
TTGCACTGGATACGACTATTC miR-129 Reverse Transcribe Primer:

(SEQ ID NO: 8)
GTCGTATCCAGTGCGAACTGTGGCGATCGGTACGGGCTACACTCGGCAA
TTGCACTGGATACGACATGCT

Cel-39 Reverse Transcribe Primer:

(SEQ ID NO: 9)
GTCGTATCCAGTGCGAACTGTGGCGATCGGTACGGGCTACACTCGGCAA
TTGCACTGGATACGACCAAGC (3) Add SYBR® Green Realtime PCR Master Mix to the PCR reaction

| | |
|---|---|
| ddH$_2$O | 7.2 μL |
| SYBR ® Green Realtime PCR Master Mix | 10.0 μL |
| Primer 1 (10 μM) | 0.4 μL |
| Primer 2 (10 μM) | 0.4 μL |
| cDNA | 2.0 μL |
| Total | 20.0 μL |

PCR Reaction Methods:

| | |
|---|---|
| 94° C. min 1 cycle | |
| 94° C. 30 sec | |
| 55° C. 30 sec | 40 cycles |
| 72° C. 1 min | |
| 72° C. 10 min | |
| 4° C. Stop | |

(4) The levels of miRNAs in serum samples of patients with ossification of posterior longitudinal ligament and healthy controls were detected and compared. The content of PCR product was calculated by ΔΔCt method. The ΔΔCt value method is based on the assumption that the number of products per cycle, the amount of the initial template is reacted to the Ct value at the exponential period of the PCR reaction, and the difference of a cycle (Ct=1) is equivalent to 2 times the number of the starting templates.

Definition: $\Delta Ct = Ct_{target} - Ct_{reference}$ $\Delta\Delta Ct = (Ct_{target} - Ct_{reference})_{treated} - (Ct_{target} - Ct_{reference})_{untreated}$ $RQ = 2 - \Delta\Delta Ct$ The statistical analysis tools in EXCEL were used to calculate the average and standard deviation of each group. T test was used between the two groups, and P<0.05 was statistically significant.

3. Results

Figure 3:
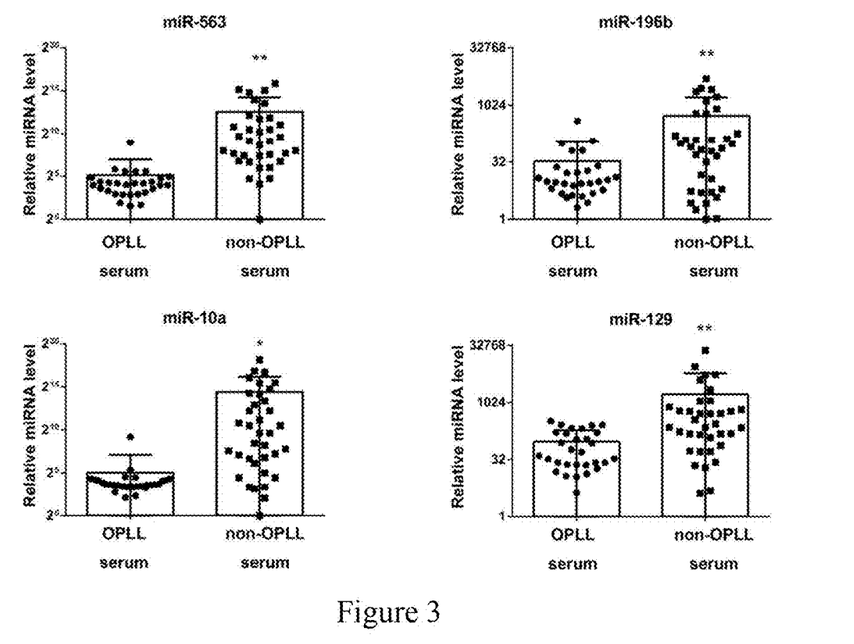
FIG. 3 The detection of serum miRNA-563, miRNA-196b, miRNA-10a and miRNA-129 in 36 OPLL patients and 30 healthy subjects in Sample Case 2. The samples with the highest CT value were taken as controls, and the relative values that is confirmed as biased were excluded by calculating the external reference cel-miR-39 content value. The results showed that the expression of miRNAs in the OPLL group was significantly higher than that in the posterior longitudinal ligament (PLL) control group. *, P<0.05; * *, P<0.01.

The levels of serum miRNA-563, miRNA-196b, miRNA-10a and miRNA-129 in case group were significantly higher than those in the control group, as shown in Table 1 and FIG. 3.

TABLE 1

Comparison of serum miRNA level between control group and case group (ΔCT) (X ± SD)

| Marker | Case(n = 36) | Control(n = 30) | P |
|---|---|---|---|
| miRNA-563 | 7.91 ± 0.35 | 0.97 ± 0.21 | 0.00002 |
| miRNA-196b | 3.22 ± 0.78 | 0.51 ± 0.49 | 0.014 |
| miRNA-10a | 5.39 ± 0.94 | 1.38 ± 0.52 | 0.0063 |
| miRNA-129 | 4.33 ± 0.82 | 1.07 ± 0.12 | 0.0052 |

The above results showed that the levels of serum miRNA-563, miRNA-196b, miRNA-10a and miRNA-129 were significantly different in the control group and the case group, suggesting that the up regulation of any of the miRNA was supportive of the ossification of the ligaments.

Sample Case 3: Screening OPLL for Patients by Detecting OPLL Specific miRNA in Serum 1. Sample Collection The case group contains 68 OPLL patients collected from June 2015 to October 2015 in the Department of Spine Center, Shanghai Changzheng Hospital. All patients were diagnosed with OPLL after CT three-dimensional reconstruction of the cervical spine. In the control group, 45 patients were admitted to outpatient department. None of the 45 patients had OPLL symptoms, signs or imaging findings. All samples were collected before treatment and the patient's consent was obtained. There was no significant difference in age, smoking, drinking and other factors between case group and control group (P>0.05).

2. Methods

Same with Sample 2.

In order to clarify the specific content of 4 kinds of miRNA in serum, we used the standard curve and absolute quantitative real-time PCR to analyze the 4 indexes mentioned above.

In addition, in order to detect the specificity and sensitivity of the above 4 miRNA indicators, the SPSS software was used to analyze the measured values, and the combined parameters were fitted by the linear regression equation. The new values of the 4 kinds of miRNA were calculated and tested.

3. Results

Figure 4:
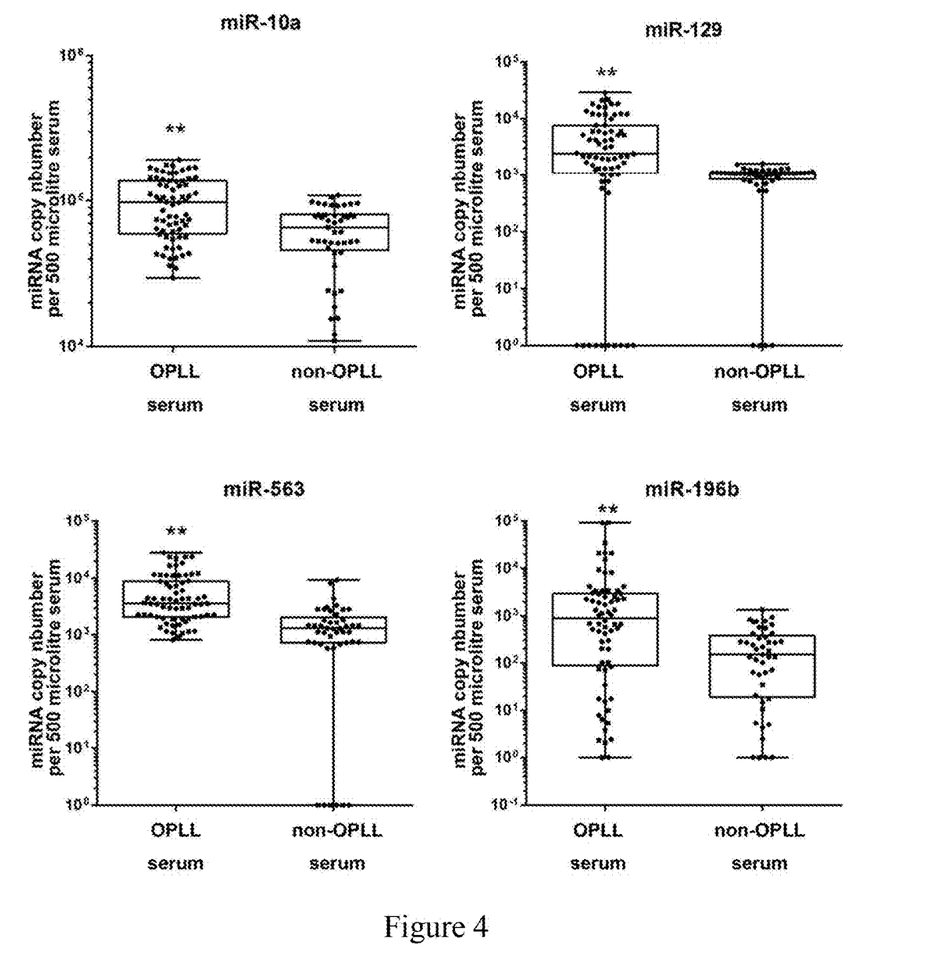
FIG. 4 The detection of serum miRNA-563, miRNA-196b, miRNA-10a and miRNA-129 in 68 OPLL patients and 45 non OPLL patients in Sample Case 3. By using the absolute quantification of real-time PCR and the standard curve, the number of miRNA copies of each sample (copy number/500 microliter serum) is obtained and analyzed. The results showed that the total expression levels of 4 miRNAs in the OPLL group were significantly higher than those in the control group. * *, P<0.01.

The expression levels of miRNA-563, miRNA-196b, miRNA-10a and miRNA-129 in the case group were significantly higher than those in the control group, as shown in FIG. 4.

Figure 5:
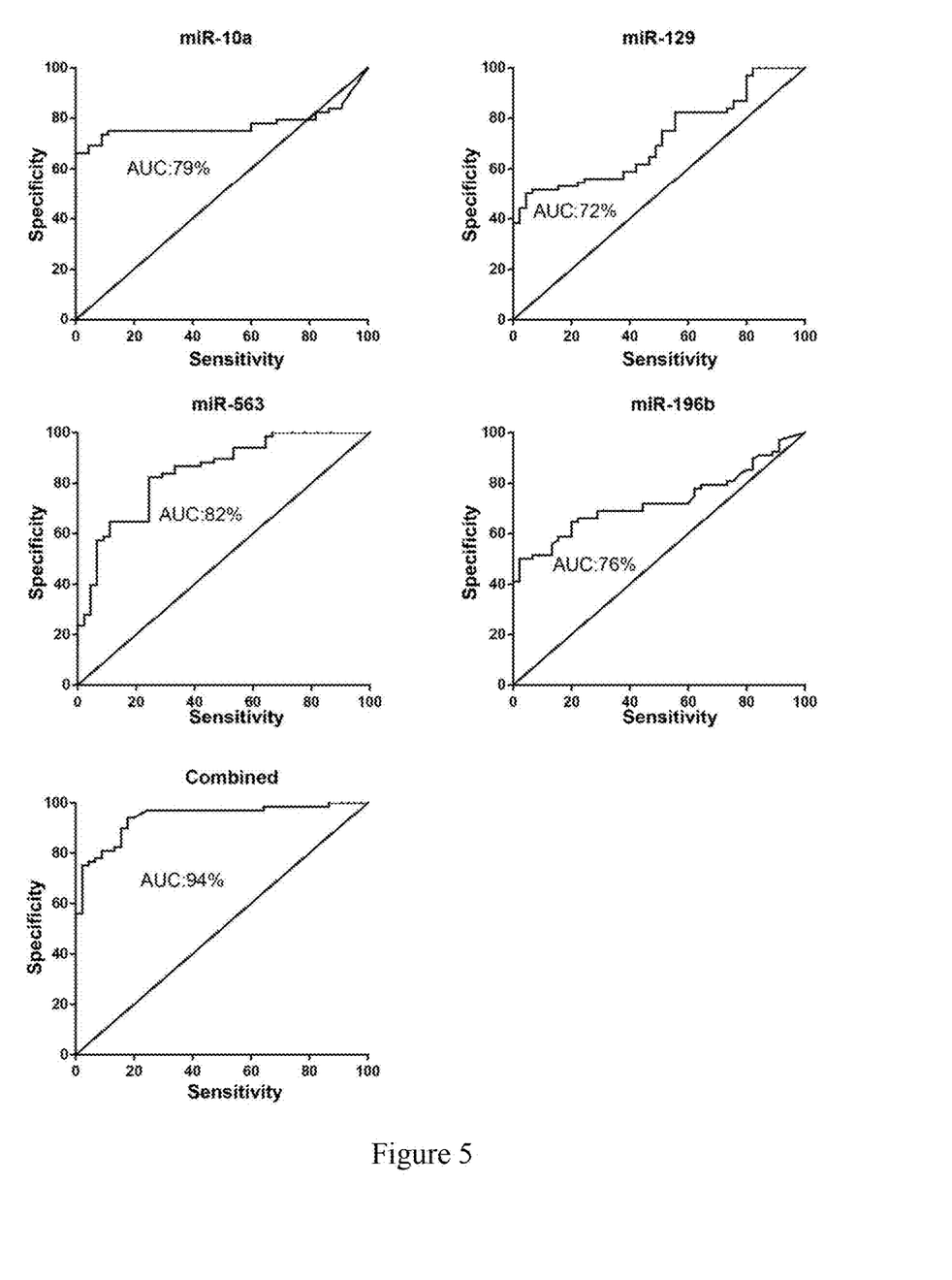

Using SPSS for ROC curve analysis, we found that the above 4 kinds of miRNA have good specificity and sensitivity, as shown in FIG. 5.

In order to combine the 4 positive indexes, we adopt linear regression equation to fit it. The results of the ROC curve analysis show that the specificity and sensitivity of the new values are higher than that of the 4 miRNAs as diagnostic marker, as shown in FIG. 5.

The better embodiments of the invention have been explained in detail above, but the invention is not limited to the embodiments described. It is familiar to the technical personnel of this field that all kinds of equivalent variants or substitutions can be made without violating the inventive spirit of the invention within the limits defined, which are included in the right of application.

What is claimed is:

1. A method of diagnosing ossification of the posterior longitudinal ligament, the method comprising:

measuring expression levels of at least one of miRNA-563 (SEQ ID NO: 1), miRNA-196b (SEQ ID NO: 2), miRNA-10a (SEQ ID NO: 3) and miRNA-129 (SEQ ID NO: 4) in a biological sample by using at least one of SEQ ID NO: 5, SEQ ID NO: 6, SEQ ID NO: 7 and SEQ ID NO: 8 as PCR primers, respectively; and calculating a risk value of [(the copy number of miRNA-563 per 500 microliter peripheral * 0.04)+(the copy number of miRNA-196b per 500 microliter peripheral venous blood serum * 0.03)+(the copy number of miRNA-10a per 500 microliter peripheral venous blood serum * 0.004)+(the copy number of miRNA-129 per 500 microliter peripheral venous blood serum * 0.05)−353], wherein the risk value is greater than 0 indicating a high risk of ossification of the posterior longitudinal ligament.

2. The method of diagnosing ossification of the posterior longitudinal ligament according to claim 1, wherein the biological sample is selected from the group consisting of a tissue, cells, blood, serum, and a body fluid.

3. The method of diagnosing ossification of the posterior longitudinal ligament according to claim 1, wherein the biological sample is serum.

4. The method of diagnosing ossification of the posterior longitudinal ligament according to claim 1, wherein the measuring step is performed by using Real-time PCR method.

* * * * *

SEQUENCE LISTING

<160> NUMBER OF SEQ ID NOS: 10

<210> SEQ ID NO 1
<211> LENGTH: 19
<212> TYPE: RNA
<213> ORGANISM: Homo sapiens

<400> SEQUENCE: 1
agguugacau acguuuccc                                                        19

<210> SEQ ID NO 2
<211> LENGTH: 22
<212> TYPE: RNA
<213> ORGANISM: Homo sapiens

<400> SEQUENCE: 2
uagguaguuu ccuguuguug gg                                                    22

<210> SEQ ID NO 3
<211> LENGTH: 23
<212> TYPE: RNA
<213> ORGANISM: Homo sapiens

<400> SEQUENCE: 3
uacccuguag auccgaauuu gug                                                   23

<210> SEQ ID NO 4
<211> LENGTH: 21
<212> TYPE: RNA
<213> ORGANISM: Homo sapiens

<400> SEQUENCE: 4
cuuuuugcgg ucugggcuug c                                                     21

<210> SEQ ID NO 5
<211> LENGTH: 70
<212> TYPE: DNA
<213> ORGANISM: Artificial sequence
<220> FEATURE:
<223> OTHER INFORMATION: miRNA-563

<400> SEQUENCE: 5
gtcgtatcca gtgcgaactg tggcgatcgg tacgggctac actcggcaat tgcactggat           60
acgacgggaa                                                                  70

<210> SEQ ID NO 6
<211> LENGTH: 70
<212> TYPE: DNA
<213> ORGANISM: Artificial sequence
<220> FEATURE:
<223> OTHER INFORMATION: miRNA-196b

<400> SEQUENCE: 6
gtcgtatcca gtgcgaactg tggcgatcgg tacgggctac actcggcaat tgcactggat           60
acgaccccaa                                                                  70

<210> SEQ ID NO 7
<211> LENGTH: 70
<212> TYPE: DNA
<213> ORGANISM: Artificial sequence
<220> FEATURE:
<223> OTHER INFORMATION: miRNA-10a

<400> SEQUENCE: 7

```
gtcgtatcca gtgcgaactg tggcgatcgg tacgggctac actcggcaat tgcactggat    60
acgactattc                                                            70

<210> SEQ ID NO 8
<211> LENGTH: 70
<212> TYPE: DNA
<213> ORGANISM: Artificial sequence
<220> FEATURE:
<223> OTHER INFORMATION: miRNA-129

<400> SEQUENCE: 8
gtcgtatcca gtgcgaactg tggcgatcgg tacgggctac actcggcaat tgcactggat    60
acgacatgct                                                            70

<210> SEQ ID NO 9
<211> LENGTH: 70
<212> TYPE: DNA
<213> ORGANISM: Artificial sequence
<220> FEATURE:
<223> OTHER INFORMATION: Cel-39 reverse transcribe primer

<400> SEQUENCE: 9
gtcgtatcca gtgcgaactg tggcgatcgg tacgggctac actcggcaat tgcactggat    60
acgaccaagc                                                            70

<210> SEQ ID NO 10
<211> LENGTH: 22
<212> TYPE: RNA
<213> ORGANISM: Caenorhabditis elegans

<400> SEQUENCE: 10
ucaccgggug uaaaucagcu ug                                              22
```